United States Patent [19]

Viehweg

[11] Patent Number: 4,871,665

[45] Date of Patent: Oct. 3, 1989

[54] PROCESS FOR THE PREPARATION OF EXOCELLULAR BIOPOLYMERS

[75] Inventor: Holger Viehweg, Langenfeld, Fed. Rep. of Germany

[73] Assignee: Henkel Kommanditgesellschaft auf Aktien, Duesseldorf, Fed. Rep. of Germany

[21] Appl. No.: 944,684

[22] Filed: Dec. 19, 1986

[51] Int. Cl.$^4$ ............................................. C12P 19/06
[52] U.S. Cl. ................................... 435/104; 435/101; 435/72
[58] Field of Search ............... 435/830, 910, 911, 101, 435/72, 102–104, 105; 106/209, 208; 252/140, 173, 174.17, 174.25, 179, 181, 315.1, 315.3, 315.4, 315.5, 315.6, 315.7, 527, 135, 174.21, 107, DIG. 1; 514/188

[56] References Cited

U.S. PATENT DOCUMENTS

| | | | |
|---|---|---|---|
| 4,226,736 | 10/1980 | Bush et al. | 252/315.4 |
| 4,352,882 | 10/1982 | Maury | 435/101 |
| 4,519,844 | 5/1985 | Chaux et al. | 252/363.5 |
| 4,618,582 | 10/1986 | Engelskirchen et al. | 435/104 |

FOREIGN PATENT DOCUMENTS

| | | |
|---|---|---|
| 0058364 | 8/1982 | European Pat. Off. |
| 0074775 | 3/1983 | European Pat. Off. |
| 0098473 | 1/1984 | European Pat. Off. |
| 0135123 | 3/1985 | European Pat. Off. |
| 0187092 | 7/1986 | European Pat. Off. |

OTHER PUBLICATIONS

Methods in Microbiology, vol. 3A, Academic Press, London, 1970.
R. L. Whistler, J. N. BeMiller (Ed): Industrial Gums, Polysaccharides and Derivatives, Academic Press, New York and London, 1973.
Ullmans Encyklopadie der technischen Chemie, 1974, vol. IV, pp. 453 et seq.
Houben–Weyl, Methoden der Organischen Chemie, 1958, vol. I/1, pp. 219–220.

*Primary Examiner*—Barry S. Richman
*Assistant Examiner*—T. J. Wallen
*Attorney, Agent, or Firm*—Ernest G. Szoke; Wayne C. Jaeschke; Henry E. Millson, Jr.

[57] ABSTRACT

Process for the preparation of exocellular biopolymers having a thickening effect in aqueous media by aerobic culture of microorganism strains forming the biopolymers in an aqueous nutrient medium present as disperse aqueous phase in a water/oil emulsion (W/O-emulsion) stable under fermentation conditions using W/O emulsifiers for emulsion formation and stabilization, in which the oil phase is used in quantities below 50% by volume, based on the mixture as a whole, and fatty acid dialkanolamides are used as the W/O emulsifiers.

11 Claims, No Drawings

PROCESS FOR THE PREPARATION OF EXOCELLULAR BIOPOLYMERS

BACKGROUND OF THE INVENTION

1. Field of the Invention

The present invention relates to a process for the preparation of exocellular biopolymers that exhibit a thickening effect in aqueous media.

2. Statement of Related Art

European Patent Application No. 0 058 364 and U.S. Pat. No. 4,618,582 relate to a process for the preparation of Xanthomonas biopolymers by aerobic culture of microorganisms of the genus Xanthomonas in an aqueous nutrient medium which is characterized in that the microorganisms are grown in a water-in-oil emulsion (W/O emulsion) which is stable under fermentation conditions. In this process, the microorganism may first be grown in an oil-free aqueous nutrient medium, a W/O emulsion subsequently formed with addition of the oil phase and fermentation continued with the W/O emulsion intact. The process is preferably carried out in the presence of W/O emulsifiers, the W/O emulsifier best being initially dissolved in the oil phase and the resulting solution subsequently mixed with the aqueous phase.

European Patent application No. 0 098 473 relates to an extended version of this process in which microorganism strains which generally form exocellular biopolymers having a thickening effect in the aqueous nutrient medium, but which do not belong to the genus Xanthomonas, are grown in W/O-emulsions of the type in question. The microorganism strains mentioned include, for example, gram-positive or gram-negative bacterial strains, fungi or algae. A corresponding teaching is given in U.S. Pat. No. 4,352,882 where particular significance is again attributed to the culture of Xanthomonas strains.

The use of W/O emulsions of the above type in the aerobic culture of, for example, xanthan-forming Xanthomonas strains affords important advantages in several respects. For example, the W/O-emulsion technique eases or eliminates the difficulties encountered in the aqueous fermentation phase of the process through the increasing degree of thickening initiated by the polysaccharide accumulating as fermentation product. Where purely aqueous nutrient media are used, yields of only 2 to 3% by weight xanthan (dry matter) may be regarded as a good result which can only be obtained by adopting special measures involving high energy consumption. By changing over to culture of the polysaccharide-forming microorganism strains in the aqueous disperse phase of W/O emulsions, the viscosity of the liquid phase in the fermenter under fermentation conditions is reduced because the viscosity of the system as a whole is primarily determined by the homogeneous oil phase. It has also been found that, by changing over to W/O emulsion systems of the above type, it is possible to obtain improved xanthan yields in the disperse aqueous phase compared with working with a purely aqueous culture medium.

European Patent Application No. 0 135 133 relates to a process for reducing the viscosity of fermentation broths by addition of a halogenated hydrocarbon and formation of corresponding W/O emulsions. In this process, non-toxic, highly halogenated, more especially perhalogenated, aliphatic hydrocarbons which are liquid under the fermentation conditions are used as the halogenated hydrocarbon phases. No emulsifiers are used. This teaching is based on the discovery that, in the previously described processes for the formation of xanthan in W/O-emulsions, the viscosity of the medium as a whole may not only not be reduced, but even increased. This danger is said to exist in particular where emulsifiers are used.

STATEMENT OF THE INVENTION

Other than in the operating examples, or where otherwise indicated, all numbers expressing quantities of ingredients or reaction conditions used herein are to be understood as modified in all instances by the term "about".

Further investigations have been unable to confirm the above reported difficulties. On the contrary, a totally different set of problems is encountered in attempts to optimize the process conditions. Two process parameters essential for economically carrying out a process such as this for the culture of microorganisms in W/O emulsions undesirably complement one another when optimized in such a way that the W/O emulsions tend to break and hence to undergo phase separation; it being difficult or impossible to re-establish the desired state of the finely disperse W/O-emulsion by simple means, such as by stirring. The two process parameters referred to above are the quantity of oil phase and the increasing enrichment of the solids phase with the extracellular polysaccharide, i.e. the yield in the disperse aqueous phase.

It is understandably desirable to work with the smallest possible quantities of oil phase in order to keep the costs of the process as a whole as low as possible. On the other hand, it is obvious that high yields of extracellular polysaccharide having a thickening effect in the disperse aqueous phase are wanted. It has now been found that the above-mentioned instability of the W/O emulsions is particularly likely to occur when the quantity of oil phase is reduced as far as possible while, at the same time, the yield of extracellular polysaccharide in the disperse aqueous phase is made as high as possible. This combination of these two parameters, which is particularly favorable so far as the economy of the process is concerend, is likely to produce serious disruption of the process through undesirable and irreversible phase separation, thus making premature termination of the culture process unavoidable.

The present invention seeks to overcome these difficulties, and does so by the surprising discovery that a special class of emulsifiers selected from the large number of known W/O emulsifiers overcomes the above discussed problems, while at the same time enabling the quantity of oil phase to be reduced to such an extent that, in terms of weight and volume, the aqueous phase clearly predominates in the mixture as a whole. Stable W/O emulsions are present even when the solids yields in the disperse aqueous phase are forced up to optimal levels.

Accordingly, the present invention relates to a process for the preparation of exocellular biopolymers having a thickening effect in aqueous media by aerobic culture of microorganism strains forming the biopolymers in an aqueous nutrient medium which is present as disperse aqueous phase in a W/O emulsion stable under fermentation conditions using W/O emulsifiers for emulsion formation and stabilization, wherein the process is carried out using an oil phase in quantities below 50% by volume, based on the mixture as a whole, and wherein fatty acid dialkanolamides are used as the W/O emulsifiers. The preferred fatty acid dialkanolamides are corresponding diethanolamides of which the fatty acid residues are mono- or poly-olefinically unsaturated. In the context of the invention, fatty acids are understood to include monocarboxylic acids, particularly of natural origin, preferably containing from 12 to 20 and more preferably from 14 to 18 carbon atoms. Known mono- or poly-olefinically unsaturated natural fatty acids are oleic acid, linoleic acid and linolenic acid.

It has been found that even very small quantities of the emulsifiers used in the process of the invention are capable of guaranteeing stable W/O emulsions even when the process is carried out with a minimum of oil phase and, at the same time, with maximal solids yield in the aqueous phase. The quantity of emulsifier used is preferably in the range of from 0.5 to 2% by weight, and more preferably in the range of from 0.7 to 1.2% by weight, based in each case on the mixture as a whole.

In the preferred embodiment, the oil phase is used in quantities below 40% by volume, based on the mixture of water and oil, quantities of oil phase of from 30 to 40% by volume being suitable. 35% by weight volume corresponds to approximately 25% by weight, again based on the mixture as a whole. Stable, comparatively readily mobile W/O emulsions are obtained with these small quantities of oil when the emulsifiers selected in accordance with the invention are used and the aeorbic culture of the exocellular polysaccharides is carried onto solids yields above 5% by weight and more especially above 7% by weight, again based on the mixture as a whole. Accordingly, the procedure according to the invention encompasses all the advantages of the emulsion technique, which include inter alia increased mobility of the reaction mixture, plus the advantage of excellent economy.

The details of the process in terms of its practical application are the same as in the prior art discussed above. Accordingly, particularly suitable oil phases are isoparaffin hydrocarbons which are liquid below the process temperature (30°±5° C.). The isoparaffin mixture marketed under the name "Isopar M" may be used with advantage in the process of the invention. Physiologically safe oil phases, particularly vegetable oil phases, are suitable for the preparation of thickening polysaccharides of food quality. The known liquid triglycerides, which are commonly referred to as edible oils, can be used herein.

One particular advantage of the process of the invention is that not only is it possible to obtain W/O-emulsions sufficiently stable under the extreme conditions of the process as well as enabling the polysaccharide-forming organism strains to be cultured under economically favorable conditions, but in addition simple separation between oil phase and aqueous phase charged with fermentation product is also possible at the end of the process despite the desired emulsion stability.

Except for the differences discussed above, the process according to the invention can be carried out in accordance with the teachings of the prior art discussed above.

The aqueous fermentation medium may be selected from those described in the literature for the particular microorganism. Suitable aqueous fermentation media are, for example, described in J. R. Norris, D. W. Ribbons (Ed.): Methods in Microbiology, Vol. 3 A, Academic Press London (1970) and in R. L. Whistler, B. N. Bemiller (Ed.): Industrial Gums, Polysaccharides and Derivatives (1973) from the same publisher.

Typical aqueous nutrient solutions contain, for example, a source of organic nitrogen, such as corn steep liquor and/or soya flour, phosphate salts, such as dialkali metal hydrogen phosphate and/or diammonium hydrogen phosphate, in addition to suitable trace elements, particularly magnesium, and, optionally, manganese, molybdenum, iron and calcium, at a pH-value above 6 and preferably from 6.5 to approximately 7. The nutrient solution additionally contains a suitable carbohydrate, which is preferably dissolved in the aqueous phase. Suitable carbohydrates are, for example, glucose, sucrose, maltose, fructose, lactose, processed inverted sugar beet molasses, invert sugar, filtered dilute quality starch or mixture of these carbohydrates. Glucose is a preferred source of assimilable carbon. The concentration of the assimilable carbohydrate compound is normally in the range of from 0.5 to 5% by weight, based on the aqueous phase. The use of relatively high concentrations of assimilable carbohydrate compounds may result in the accumulation of toxic secondary products and hence in an inhibition of the growth of the microorganism. Low molecular weight metabolism products unsuitable for many applications may also be formed. In some cases, fermentation is even prematurely terminated.

However, the assimilable carbohydrate compound may be added in portions or continuously during the fermentation process, so that, ultimately, considerably higher glucose concentrations can be reacted. One particular embodiment of the invention comprises using n-paraffins containing more than 10 C-atoms as the oil phase and, at the same time, culturing microorganisms which are capable of utilizing them as a source of assimilable carbon. Microorganisms such as these are known from the genera Corynebacterium, Brevibacterium and Mycobacterium, for example C. viscosum or M. lacticolum.

In every case, the incubation temperature is preferably around 30° C., for example 30°±10° C. Fermentation can be carried out over a period of up to about 100 hours or even longer.

Suitable Xanthomonas organisms capable of forming exocellular heteropolysaccharides are derived, for example, from the following Xanthomonas species: Xanthomonas campestris, Xanthomonas phaseoli, Xanthomonas malvacearum, Xanthomonas translucens, Xanthomonas carotae, Xanthomonas hederae, Xanthomonas papavericola, Xanthomonas begoniae, Xanthomonas incanae, Xxanthomonas vasculorum and Xanthomonas vesicatoria. Strains of Xanthomonas campestris are particularly suitable, as are strains of Xanthomonas fragaria, Xanthomonas gummisudans, Xanthomonas manihotis and Xanthomonas vasculorum. Other suitable microorganism strains which are capable of forming exocellular heteropolysaccharides, but which do not belong to the genus Xanthomonas are listed in detail in the above-cited European Patent Application No. 0 098 473.

Suitable microorganisms which can form exocellular heteropolysaccharides can be derived, for example, from the following bacteria and yeast species or genera:
Bacteria:
Bacillus spp.
Leuconostoc spp.
*Streptococcus mutans*
Streptococcus spp.

Azotobacter spp.
Rhizobium spp.
*Escherichia coli*
*Klebsiella aerogenes*
*Azotobacter xylinum*
*Arthrobacter viscosus*
*Pseudomonas aeruginosa*
Achromobacter spp.
*Alcaligenes faecalis var. myxogenes*
Agrobacterium spp.
Erwinia spp.
*Sphaerotilus natans*
Yeasts:
Rhodotorula spp.
Pichia spp.
*Pachysolen tannophilus*
Lipomyces spp.
*Hansenula capsulata*
*Hansenula holstii*
Cryptococcus spp.
*Torulopsis molischiana*
*Torulopsis pinus*
*Aureobasidium pullulans*

Fungi are suitable, although less desirable, for growth in water-in-oil emulsions. In particular, fungi that grow in filaments, such as *Sclerotium delphinii*, can cause difficulties. Based on their slow rate of growth and their need for light, algae which form extracellular polysaccharides are also less desirable for use in this process. The selection of the microorganism depends mostly on the desired bipolymer. However, microorganisms which are pathogenic to humans, animals or plants are less suitable because they must be handled in closed systems. When choosing between equivalent alternatives, those skilled in the art will take into consideration the efficiency thereof, such as the growth rate.

To form the W/O emulsion, the cultured nutrient solution and the oil phase, in which the emulsifier used is best dissolved beforehand, are mixed together and the resulting mixture mechanically agitated or mixed with sufficient intensity. The preferred embodiment of the process of the invention comprises culturing the microorganisms within the actual W/O emulsion in fermenters equipped with intensive mixing elements. According to the invention, the intensive mixing effect of such elements may be used to maintain and guarantee the state of the W/O emulsion in the fermenter, even where relatively simple phase separation occurs when the contents of the fermenter come to a standstill.

The agitated contents of the fermenter are gassed in the usual way with oxygen or with an oxygen-containing gas, particularly air. The oxygen is transferred via the oil phase to each individual particle emulsified in disperse phase of the aqueous microorganism-containing nutrient solutionso that transfer is disrupted far less, even in later stages of the process, than in conventional processes.

If necessary, the growth-promoting constituents of the nutrient solution may be replenished in portions or continuously. Thus, it is possible for example to gradually add the compounds containing assimilable carbon, such as glucose, to the reaction mixture.

Uniform distribution can be obtained by directly introducing these nutrients into the intensively mixed fermenter. The same applies to other constituents of the aqueous nutrient solutions, for example trace elements, or the addition of other necessary reactants, for example bases, for regulating the pH-value of the disperse aqueous phase.

Culturing is continued until the desired yield is obtained or until formation of the biopolymer decreases or comes to a standstill. In the batch process, the oil phase and the biopolymer-containing disperse phase are generally separated, depending on the envisioned application of the product, after which the polysaccharide can be separated off from the aqueous phase and purified in the usual way. The W/O-emulsions may be broken by the methods normally used in chemical process technology, cf. for example Ullmann Enzyklopadie der technischen Chemie 1975, Vo. IV, pages 453 et seq and Houben-Weyl, Methoden der Organischen Chemie 1958, Vol. I/1, pages 219–220. Accordingly, separation of the emulsion can be effected by addition of emulsion-breaking substances, optionally by the application of mechanical forces, such as vibration, impact or pressure; by increasing temperature; by dilution; or by concentration of the outer phase by evaporation, and/or other known measures. The destruction of emulsions by addition of suitable chemical compounds, so-called demulsifiers, is particularly well-known in process technology. Several emulsion breakers are commercially available, cf. for example Houben-Weyl, loc. cit. Separation may be followed by standard purification steps, for example washing out the biopolymer-containing aqueous phase with suitable solvents.

In one particular embodiment of the process according to the invention, a partial stream of the fermenter contents may be branched off in batches or continuously, worked up and, if desired, at least partly returned. The partial stream branched off may be used for example for the addition of reaction aids or even for the addition of fresh supplies of microorganism. At the same time, end product may be removed in batches or continuously from the fermenter through a sidestream. This enables the process of the invention to be carried out continuously; the course of the process being controllable in the required direction by regular control of the aqueous phase containing the biopolymer. This in turn opens up new technically advanced possibilities over the single-stage batch process hitherto applied in practice.

The polysaccharide is isolated from the aqueous phase in known manner, for example by precipitation and drying. The aqueous phase may first be sufficiently heated, for example to temperatures above 100° C., and immediately cooled again to kill off the microorganisms present and if necessary to improve the viscosity of the biopolymer. The biopolymer is then obtained by precipitation, for example with alcohols, subsequent filtration, and drying. Washing stages for purifying the product may be included in known manner.

The invention will be illustrated, but not limited, by the following examples.

EXAMPLES

EXAMPLE 1

Xanthomonas cpmpestris NRRL-B-1459-A was aerobically cultured at 28° C. in a 15 liter fermenter (filling volume 10 l). The fermenter was inocculated with a 24 hour-old preculture.

Nutrient medium of the main culture:

| | |
|---|---|
| Corn steep liquor | 10 g/l |
| Soya flour | 6 g/l |

| -continued | |
|---|---|
| Na$_2$HPO$_4$ × 12 H$_2$O | 0.9 g/l |
| (NH$_4$)$_2$HPO$_4$ | 0.8 g/l |
| MgSO$_4$ × 7 H$_2$O | 0.2 g/l |
| Oil: Isopar M* | 250 g/l |
| Emulsifier: | |
| Linoleic acid diethanolamide | 8 g/l |
| Rotational speed | 2200 min$^{-1}$ |
| Air | 1 VVM |

*Trademark of Esso Chemie for an isoparaffin mixture boiling in the range of 200 to 250° C.

After preparation of the culture solution, the reactor was sterilized and inoculated. The glucose was continuously introduced during the fermentation so that the concentration remained at around 10 g/l. The pH-value was kept constant at pH 7.0 with potassium hydroxide. After a fermentation time of 30 hours, the stirrer was briefly stopped and the externally sterilized oil added with the emulsifier. After addition of the oil, fermentation was continued in the same way as before.

After a culture time of around 160 hours, the xanthan concentration was 61 g/l.

EXAMPLE 2

A second test was carried out in the same way using the Xanthomonas campestris strain ATCC 31 602. In this case, however, the commercial product "Comperlan VOD" was used as emulsifier. Comperlan VOD is a product marketed by Henkel KGaA, Duesseldorf, Germany, and consists of fatty acid diethanolamide based on vegetable oils.

When fermentation was stopped in the 110th hour, the xanthan concentration was measured at 65 g/l.

COMPARISON EXAMPLE

A comparison fermentation using another emulsifier was carried out under otherwise the same conditions. In this case, an emulsifier marketed by Henkel KGaA under the name "Dehymuls F", a mixture of relatively high molecular weight fatty acid esters, was used instead of linoleic acid diethanolamide.

After preparation of the emulsion, fermentation had to be stopped because the emulsion did not remain stable so that no further xanthan formation was possible. The xanthan concentration after termination was 20 g/l.

What is claimed is:

1. In a process for the preparation of exocellular biopolymers having a thickening effect in aqueous media by aerobic culture of microorganism strains that form the biopolymers in a culture medium comprising an aqueous nutrient medium which is present as a disperse aqueous phase in an oil phase in a water/oil emulsion stable under fermentation conditions, the improvement wherein in the culturing step (a) the oil phase is used in quantities below 50% by volume, based on the culture medium, and (b) an emulsifying effective quantity of at least one fatty acid dialkanolamide is employed as an emulsifier.

2. The process of claim 1 wherein the fatty acid dialkanolamide is a mono- or poly-olefinically unsaturated fatty acid diethanolamide.

3. The process of claim 1 wherein the emulsifier is used in a quantity of from about 0.5 to about 2% by weight, based on the culture medium.

4. The process of claim 1 wherein the emulsifier is used in a quantity of from about 0.7 to about 1.2% by weight, based on the culture medium.

5. The process of claim 1 wherein the oil phase is at least one isoparaffin hydrocarbon liquid at 25° C.

6. The process of claim 1 wherein the oil phase is a liquid triglyceride.

7. The process of claim 6 wherein the liquid triglyceride is an edible oil.

8. The process of claim 1 wherein the oil phase is used in a quantity of from about 30 to about 40% by volume, based on the volume of culture medium.

9. The process of claim 1 wherein the process is carried out until at least 5% by weight yield of biopolymer is obtained.

10. The process of claim 1 wherein the microorganism is of the genus Xanthomonas.

11. The process of claim 1 wherein the microorganism produces a polysaccharide biopolymer.

* * * * *